(12) United States Patent
Calvert et al.

(10) Patent No.: US 6,739,465 B1
(45) Date of Patent: May 25, 2004

(54) ORAL FEEDING BOTTLE

(76) Inventors: John Richard Calvert, 13 Hemnall Street, Epping, Essex (GB), CM16 4LS; Martyn Omar Rowlands, 90D Hamnall, Epping, Essex (GB), CM16 4LS; Michael Anthony Hobbs, 79 Monklow Drive, Woodford GreenEssex (GB), 1G8 0LD ( * ) Notice: Subject to any disclaimer, the term of this patent is extended or adjusted under 35 U.S.C. 154(b) by 0 days.

(21) Appl. No.: 09/743,427

(22) PCT Filed: Jul. 7, 1998

(86) PCT No.: PCT/GB98/01784

§ 371 (c)(1),
(2), (4) Date: Mar. 8, 2001

(87) PCT Pub. No.: WO00/01344

PCT Pub. Date: Jan. 13, 2000

(51) Int. Cl.[7] ............................................. A61J 9/00
(52) U.S. Cl. .................... 215/11.6; 215/11.1; 215/390
(58) Field of Search .................... 215/11.1, 11.6, 215/390, 386

(56) References Cited

U.S. PATENT DOCUMENTS

| | | | | |
|---|---|---|---|---|
| 1,466,190 A | * | 8/1923 | Richmond | 215/390 X |
| 1,623,544 A | * | 4/1927 | Kushner | 215/11.6 X |
| 2,167,284 A | * | 7/1939 | Sauder | 215/11.6 |
| 2,843,281 A | * | 7/1958 | Gallois | 215/11.6 X |
| 3,273,703 A | * | 9/1966 | Stribley | 215/11.6 |
| 3,373,864 A | * | 3/1968 | Barton et al. | 215/11.6 |
| 3,531,009 A | | 9/1970 | Saperstein | |
| 3,747,791 A | * | 7/1973 | Fouser | 215/11.1 |
| 3,902,618 A | | 9/1975 | Guerster et al. | |
| 4,703,863 A | * | 11/1987 | Kohus | 215/11.1 |
| 4,815,615 A | * | 3/1989 | Phlaphongphanich | 215/11.1 |
| 5,112,628 A | * | 5/1992 | Conrad | 215/11.6 X |
| 5,318,191 A | * | 6/1994 | Pomales et al. | 215/11.6 |
| 6,123,065 A | * | 9/2000 | Teglbjarg | 215/11.1 X |

FOREIGN PATENT DOCUMENTS

| | | |
|---|---|---|
| EP | 0 658 349 A1 | 6/1995 |
| FR | 1038319 | 9/1953 |
| FR | 2 684 549 | 6/1993 |
| GB | 678550 | 9/1952 |
| GB | 2 247 624 A | 3/1992 |

\* cited by examiner

*Primary Examiner*—Tri M. Mai
(74) *Attorney, Agent, or Firm*—Fish & Richardson P.C.

(57) ABSTRACT

An oral feeding bottle includes a feed container with an open end and surfaces adapted to come into contact with a liquid feed in the container, a teat releasably connected to the open end and adapted to contact both the liquid feed and a person or animal feeding from the bottle, and a cap with two modes of operation, where in the first mode, the teat is connected to the container and the cap is adapted to fit over, enclose the teat, and be releaseably connected to the feed container, and where in the second mode, the cap includes a means for stowing the teat in a non-dispensing position spaced from the container, where the teat and the surfaces that contact the liquid feed are in fluid communication so that the teat and the feed container are sterilized with a fluid sterilizing medium disposed in the container.

23 Claims, 9 Drawing Sheets

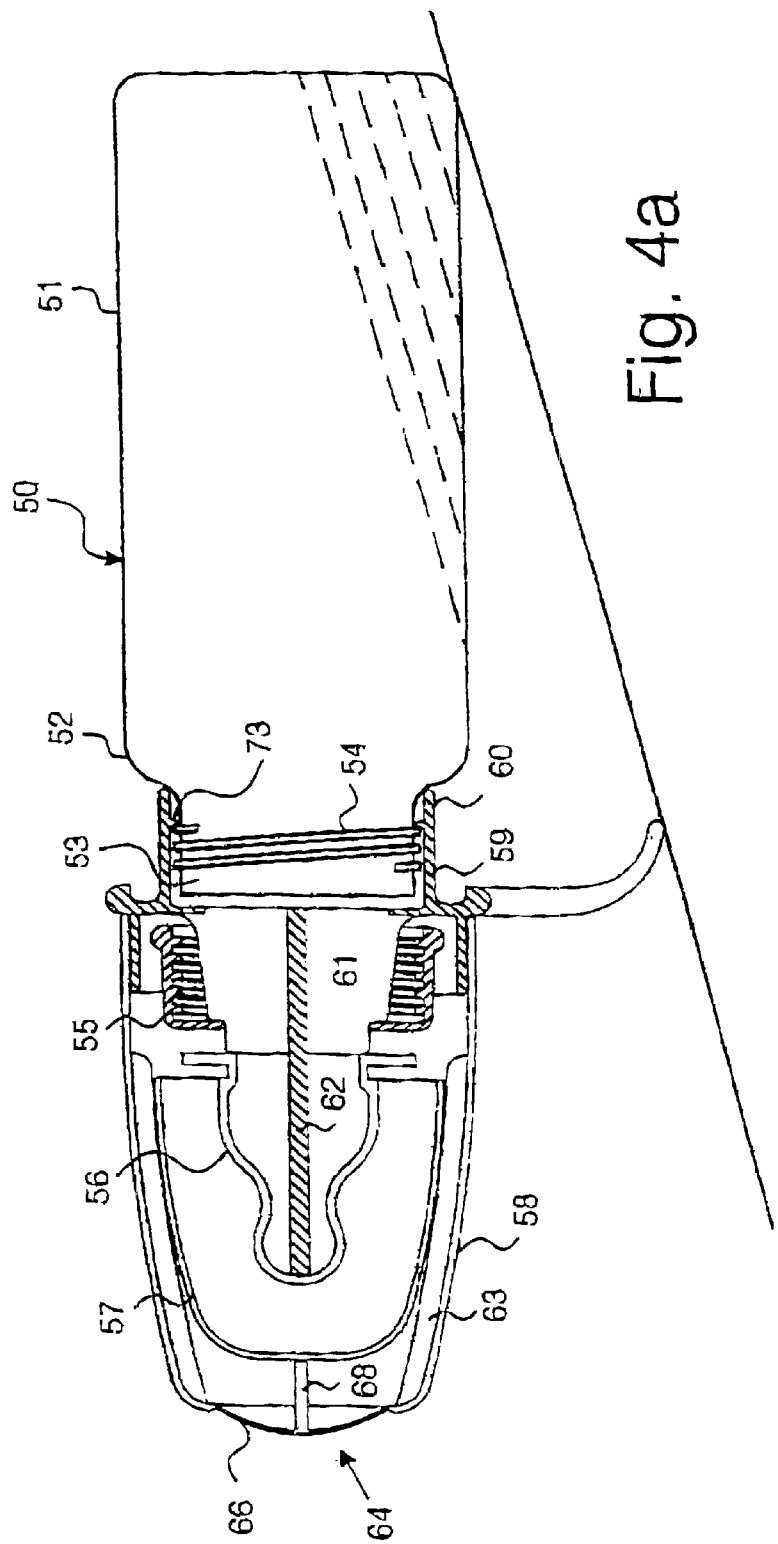
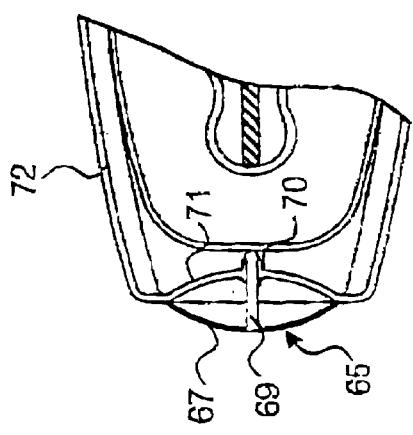
Fig. 4a
Fig. 4b

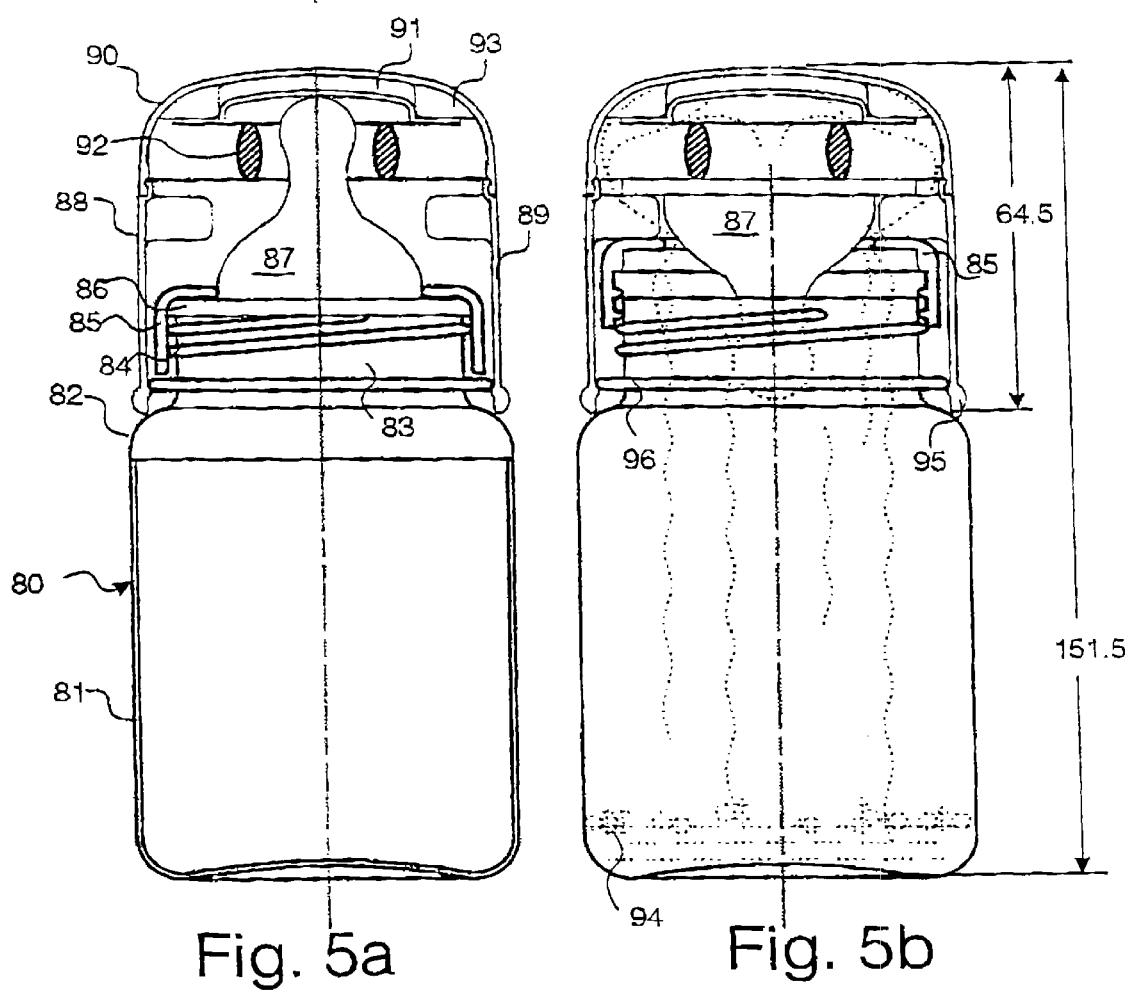

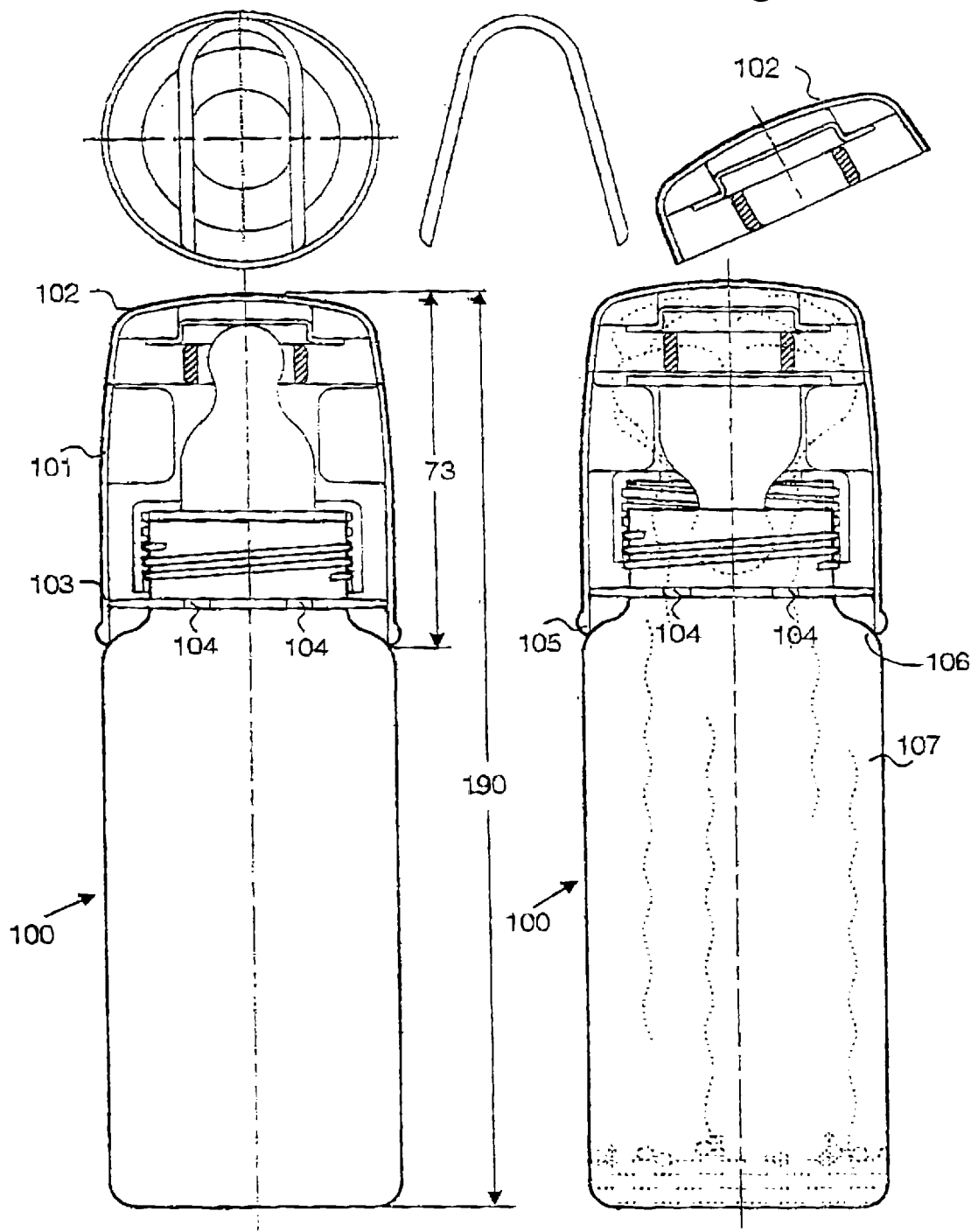

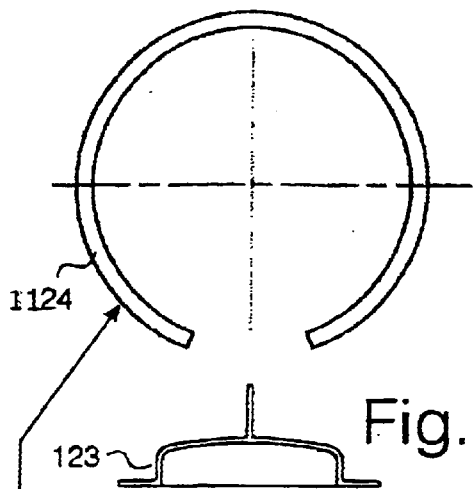
Fig. 7d
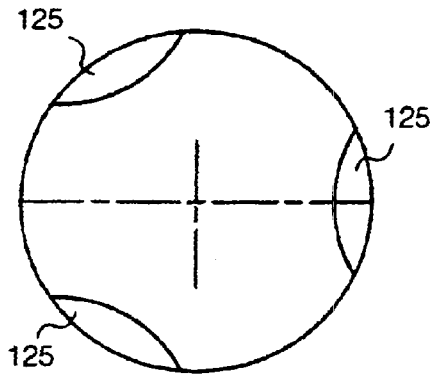
Fig. 7c
Fig. 7e
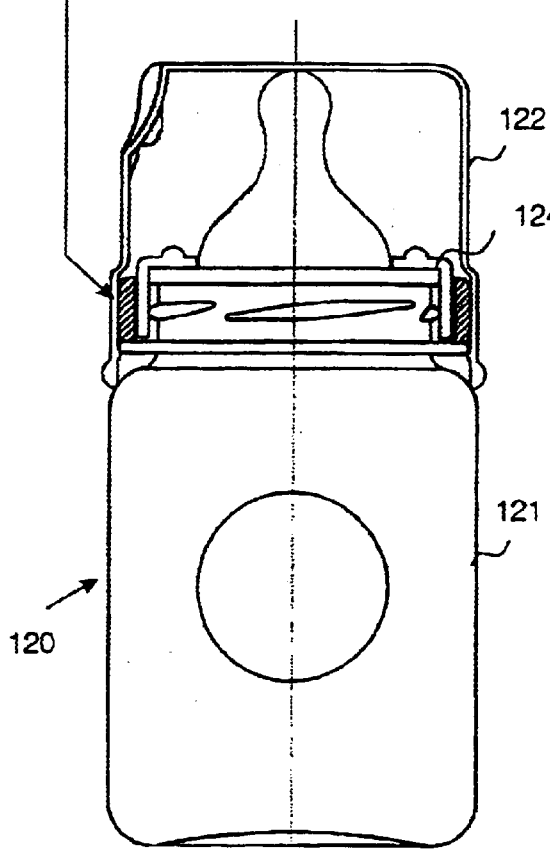
Fig. 7a
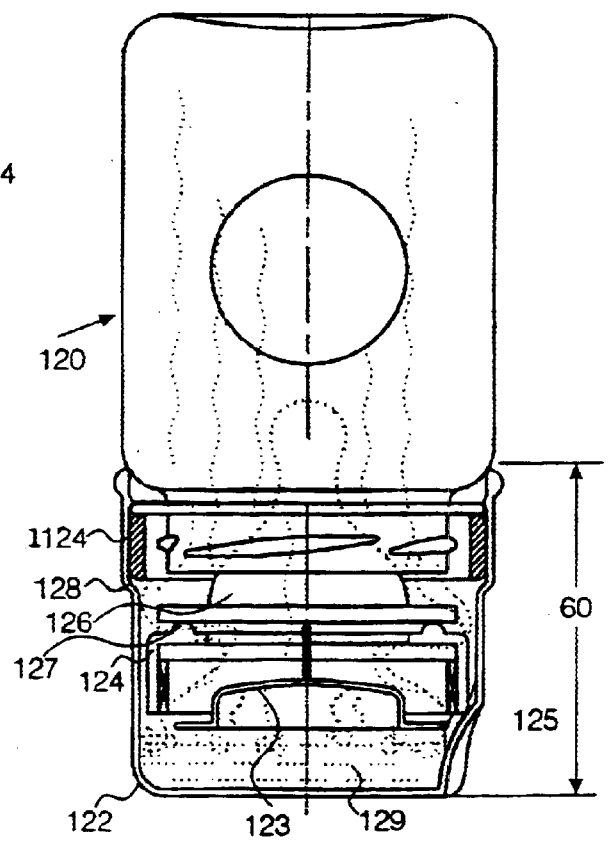
Fig. 7b

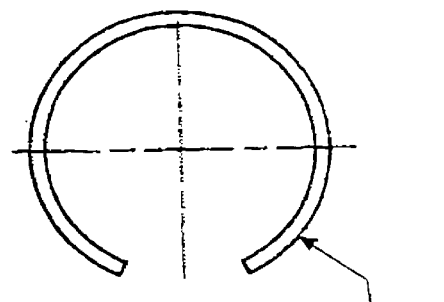
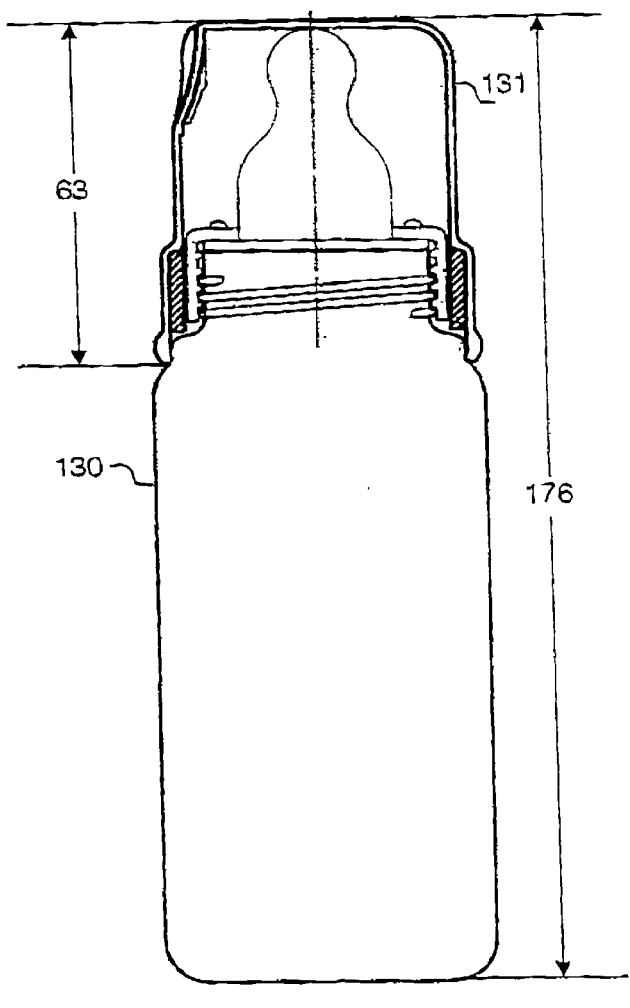
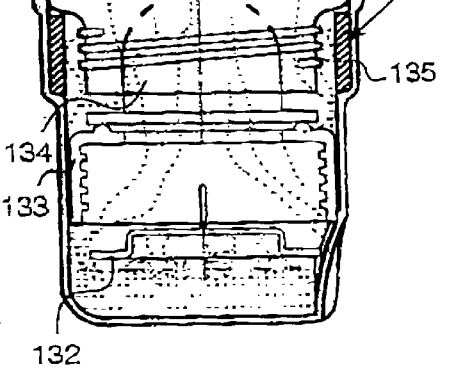
Fig. 8c
Fig. 8a    Fig. 8b

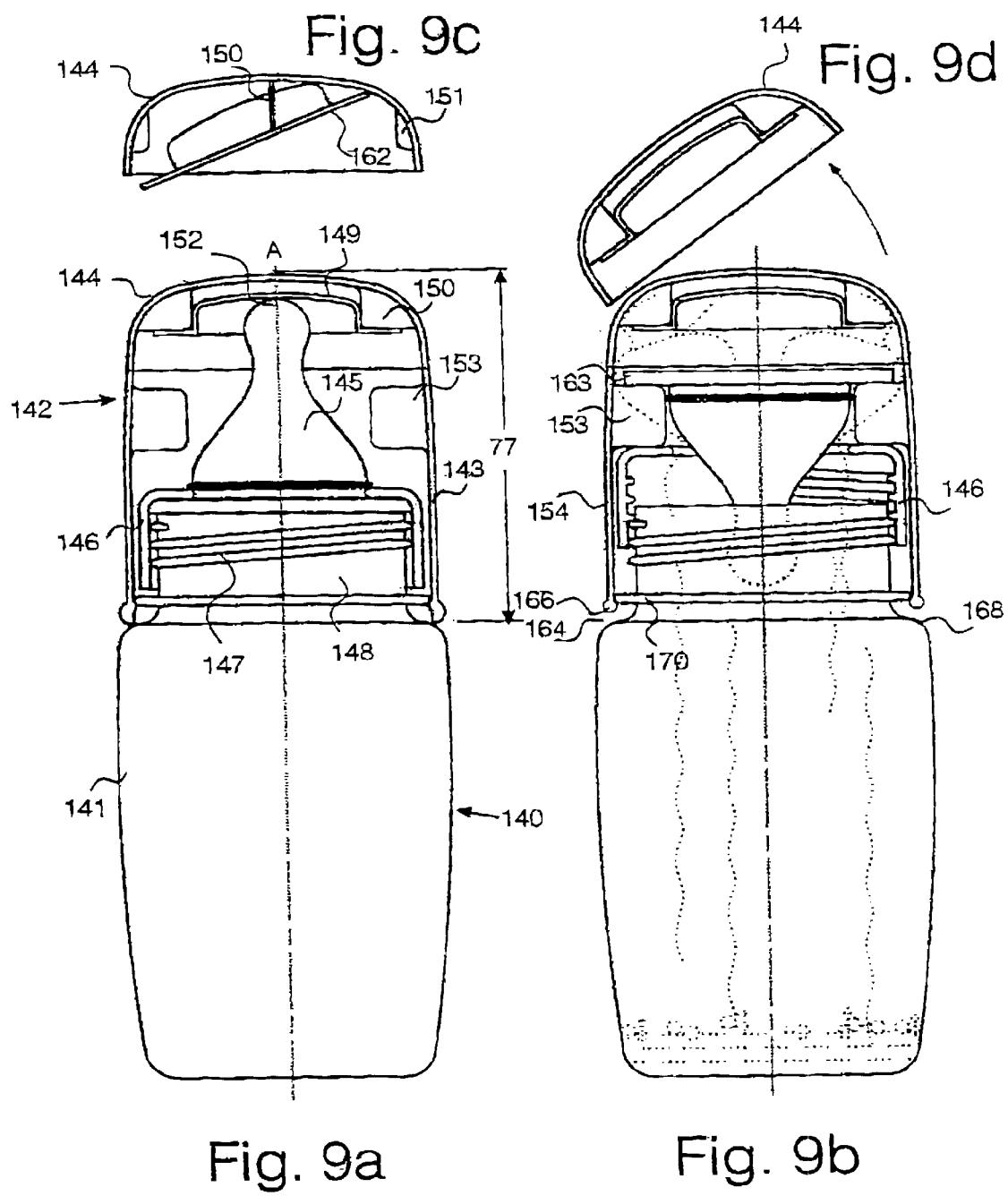

ORAL FEEDING BOTTLE

FIELD OF THE INVENTION

This invention relates to oral feeding bottles and more particularly to a novel sterilisable oral feeding bottle and a method of sterilisation therefor.

BACKGROUND OF THE INVENTION

There are a wide variety of infant oral feeding bottles on the market. In general, their components comprise a feed container, which is usually transparent and made of glass or plastics material, the container having at its open end a neck to which is releasably connected a feed dispensing means, usually a teat, formed of rubber or plastics material. The feed container is usually provided with a screw thread about its neck, and a threaded retaining collar is used to connect the feed dispensing means to the container.

Other components which can form part of a conventional infant oral feeding bottle include a sealing disc, which is used to cover the open end of the feed container when the feeding bottle is not in use, and a dormal cap which is a press fit on the retaining collar and is shaped in order to accommodate and protect the feed dispensing means when it is connected in its operative position.

After each feed it is important that the infant oral feeding bottle component parts should be sterilised, and a wide variety of sterilisers and sterilisation methods have been proposed. The term "sterilisation" for this purpose is used to indicate a certain standard which is generally accepted as being capable of killing the harmful bacteria that might be dangerous to young babies if such bacteria were to come into contact with the feed. This standard is more correctly called "disinfection". Most of the products and methods which have been proposed, however, are called respectively "sterilisers" and "sterilisation" and this is the term which will henceforth be used in this document.

It is generally accepted that moist heat, steam or water at 80° C. for one minute on the surface of the components of the feeding bottle is sufficient to kill harmful bacteria and to sterilise the bottle components for use.

One method of sterilisation which is commonly used is to use a chemical bath into which the components are totally submerged for at least 30 minutes. This has the disadvantage that it takes a long time, and the recommended time period has to be restarted if further components are added to those already submerged. In addition, all traces of the chemical have to be removed as the chemical is harmful to ingest. For this reason, it is recommended that the bottle components are rinsed in recently boiled water after sterilisation, which can itself give rise to possible to re-infection.

Electrical sterilisers are also commercially available, and typically these can comprise an enclosed container capable of receiving six feeding bottles in disassembled state. A predetermined quantity of water, usually 30 ml or 40 ml is placed on a heater dish and boiled dry. The steam created sterilises the surfaces of all the feeding bottle components. The process takes from five to ten minutes, and is thus quicker than the chemical method, and probably more reliable, but does require a relatively expensive electrical device. The device is considerably more expensive than an electrical kettle, for example.

A further method which has been proposed is to place all of the feeding bottle components into a vessel together with a quantity of water, and to boil the water by placing the container in a microwave oven for a specific period sufficient to create steam within the vessel. The process takes approximately 10 minutes as the bottle components and the vessel itself also absorb heat, thus delaying the rise in temperature of the water.

Other sterilisation methods use a carrier for the feeding bottle components which is placed in a container over a pan of water so that the steam rises into the container as the pan of water is brought to the boil, eventually sterilising all the components. This is a fairly lengthy procedure. Alternatively, all the feeding bottle components are placed in a pan of boiling water and the water kept boiling for some time. If, in this latter method, some of the components are made of plastics that float or contain air bubbles that allow them to float, it cannot be established exactly how long they must stay in the boiling water in order to sterilise them.

As will be seen from the above, all of the known sterilisation methods use either expensive equipment, or potentially harmful chemicals, or take a considerable time to sterilise the components of a feeding bottle.

BRIEF SUMMARY OF THE INVENTION

According to the present invention, instead of placing water in a separate vessel, and then loading the feeding bottle components into this vessel, closing it and boiling the water either by an electrical heated dish or by a microwave oven, the sterilising fluid is introduced into the feed container to be sterilised, or into a novel cap which is releasably connectable to the open end of the feed container.

In a first aspect, the invention provides an oral feeding bottle, comprising a feed container having an open end and a feed dispensing means releasably connectable therewith, and a cap, adapted to fit over the open end of the feed container and to be releasably connected to the feed container, the cap being provided with means for stowing the feed dispensing means when the feed dispensing means is released from the container, whereby, when the cap is connected to the container, sterilisation of the feed dispensing means and the feed container can be carried out with a sterilising medium.

In another aspect, the invention provides a method for sterilising an oral feeding bottle, the bottle comprising a feed container having an open end and a feed dispensing means releasably connectable therewith, wherein a sterilising chamber is formed from the feed container and a cap releasably engagable therewith, the chamber so formed enclosing the feed dispensing means, whereby sterilisation of the feed dispensing means and the interior of the feed container can take place using a sterilising medium disposed within the chamber.

In a further aspect, the invention provides a cap for an oral feeding bottle, the bottle comprising a feed container having an open end and a feed dispensing means releasably connectable therewith, the cap being adapted to fit over the open end of the container and to be releasably connectable therewith, wherein the cap is provided with means for stowing the feed dispensing means when the feed dispensing means is released from the container and the cap is connected to the feed container, whereby sterilisation of the feed dispensing means and the interior of the feed container can be carried out with a sterilising medium.

The feed container comprises a hollow body, which for example, can be cylindrical or square shaped in cross-sections. The feed container may be transparent and formed from glass or a plastics material, and can be provided with a neck and shoulder at its open end. The feed container can also desirably be provided with a graduated scale indicating the volume of the contents.

The open end or neck of the feed container is preferably provided with a screw thread co-operable with a screw threaded retaining collar for connecting the feed dispensing means to the feed container. The feed dispensing means normally is a teat or spout which can be formed from a rubber or plastics material. The teat or spout can be provided with a circumferential flange which is gripped by the retaining collar and serves to secure the teat to the open end of the feed container.

Other optional components of the oral feeding bottle of the invention include a sealing disc, which can co-operate with the retaining collar to seal the feed container, optionally with the teat or spout inverted therein.

In a yet further aspect of the invention a pair of tongs are provided for handling the sterilised components of the oral feeding bottle. According to this aspect of the invention, an oral feeding bottle comprises a feed container having an open end, feed dispensing means releasably connectable therewith, a cap adopted to fit over the open end of the feed container, and a pair of tongs adapted to be stowed in the cap in such a manner that the cap can still be connected to the feed container. Finally, in certain embodiments a dormal cap of conventional type can also be used.

In a particularly preferred embodiment of the invention, all the de-mountable components of the oral feeding bottle other than the feed container can be stowed in the cap of the invention. Preferably the cap is adapted to be a press fit onto a shoulder, or onto one or more peripheral projections, on the feed container.

The cap of the invention can take the place of the conventional dormal cap normally supplied with an oral feeding bottle, or can be adapted to receive a conventional dormal cap stowed therein. Preferably the cap of the invention is adapted to be releasably connectable to the feed container in such a manner that the threads surrounding the open end or neck of the feed container can also be treated by the sterilising medium and can be protected from contamination until all the components of the oral feeding bottle are re-assembled. Assembly of the components of the oral feeding bottle can conveniently be carried out using the tongs previously referred to, without the need to handle any of the components.

The means for stowing the feed dispensing means and other components of the oral feeding bottle within the cap can, for example, comprise webs, projections, indents, ledges, shoulders and other shaped configurations for receiving, and preferably retaining, components of the oral feeding bottle. It will be appreciated that the means for stowing the components within the cap are preferably as simple as possible, and should, as far as possible, be devoid of re-entrant and undercut portions which might provide regions difficult to sterilise or make the cap difficult to mould. It will also be appreciated that, whilst the means for stowing the components of the oral feeding bottle are disposed within the cap of the invention, the components when stowed need not be wholly within the cap and, for example, the teat may protrude into the interior of the feed container.

In another preferred embodiment of the invention, the tongs may, but need not necessarily, be omitted, and the components stowed within the cap in such a manner that the cap can be pushed down over the open end of the feed container to bring the retaining collar into abutment with the neck of the feed container. In the embodiment, the cap and collar can, for example, be turned in order to connect the collar to the neck of the feed container.

The collar and neck portion can, for example, be provided with inter-engaging threads. The components can be so assembled in the cap that, for example, the collar connects either the feed dispensing means, or the sealing disc, or both, to the neck of the feed container. Thus the cap can be used to offer the collar, together with the feed dispensing means, or the sealing disc, or both, to the feed container for connection, without the need to handle any of these components.

It is important that, when the components of the oral feeding bottle are stowed in the cap of the invention, as far as possible all their surfaces should be freely accessible to the sterilising medium.

In a preferred embodiment of the invention, sterilisation of the oral feeding bottle is carried out using a microwave oven. Thus, for example, a small quantity of water can be disposed within the feed container or the cap of the invention, and the cap with the other components of the oral feeding bottle stowed therein, and the feed container, can be assembled together. The bottle can then be placed within a microwave oven, either upright, or tilted on its side, or inverted, and the water boiled by activating the oven for a specific time, in general, about 10 ml to 100 ml, preferably 15 ml to 30 ml, for example, about 20 ml of water is used in the method of the invention, and boiled for from 1 to 5 minutes per bottle. Although less preferred, it would be possible to use a sterilising chemical fluid in place of the boiling water, thereby avoiding the use of a microwave oven. However, a larger quantity of fluid may need to be used, and the time taken would be much longer.

From the above description it can be seen that the cap of the invention, when attached to the feed container, in effect forms a sterilising chamber. Any number of oral feeding bottles according to the invention, each containing the requisite amount of water, can be placed in a microwave oven and sterilised by boiling the water. When the microwave oven is activated, the boiling water creates steam which is able to surround the components stowed in the cap of the invention, and preferably also the thread around the open end or neck of the feed container as well as sterilising the interior of the feed container itself. Thus all the components that are in direct contact with the feed to be given to the infant can receive the moist heat in order to sterilise their surfaces. The only areas that are not fully exposed to the sterilising moist heat are the outside base of the bottle and the outside of the cap of the invention. These areas are in any case likely to be subject to contamination by handling, or storage in a refrigerator, after sterilising in any conventional steriliser.

It can be seen that, in the method of the invention, the cap of the invention can keep all of the sterilised components of the oral feeding bottle and their surfaces protected until the feed is disposed in the feed container. Even at this stage, by use of the tongs as previously discussed, the teat retaining collar and sealing disc need not be handled, but can be placed in the desired position using the tongs.

In the preferred method of the invention, in which sterilisation is carried out using steam, preferably by placing the oral feeding bottle within a microwave oven, the bottle is preferably provided with means for venting excess steam and preventing a build up of pressure within the sterilising chamber formed by the feed container and the cap of the invention. The venting means can comprise, for example, one or more small holes, or apertures in the wall of the cap of the invention. Alternatively, a discontinuity can be provided, in either the cap or the exterior of the feed container, whereby steam can escape between the cap and the exterior wall of the feed container. In one embodiment, for example, the feed container can be provided with a projecting lip or ridge over which the cap of the invention is a press fit. Discontinuities or recesses in either the cap or the lip at the point of engagement can provide convenient venting means for escape of excess steam and also allow any remaining water to be emptied from the feeding bottle after sterilisation. Alternatively, the cap may be provided with a valve for this purpose.

In a further embodiment, the cap of the invention can be provided with one or more projecting legs or ledges at one or more sides thereof, whereby the oral feeding bottle can be laid down at an angle to the horizontal to minimise the possibility of water draining out of the neck of the feed container during the sterilisation procedure. This would be more likely to occur if the bottle were laid completely horizontally, as may be necessary in some smaller microwave ovens. In certain embodiments, the water to be boiled can be placed in the cap of the invention, and the bottle assembly inverted to stand on the cap, with the feed container extending above it.

In another preferred embodiment, the cap of the invention can be provided with an additional grid in order to receive and retain the components to be stowed. This embodiment is particularly useful if the feeding bottle has a conventional dormal cap and enables the cap of the invention to be used with a conventional oral feeding bottle. In this embodiment, the cap of the invention may be provided with an ejector device to enable the components of the oral feeding bottle, particularly the conventional dormal cap, to be ejected from the cap of the invention, for assembly in the normal way. The grid can also, if desired, carry the projecting leg or ledge for supporting the bottle when laid on its side. The grid can be, for example, a press fit, a screw fit, or an interference fit in the cap.

In order to re-assemble the components of the bottle without introducing contamination it is preferred to use a pair of tongs as previously described. When the tongs are stowed in the cap of the invention, it is desirable that they can be readily accessed, preferably without first removing the other components.

Accordingly, in another preferred embodiment, the cap of the invention is in two separable parts, preferable comprising a body portion and a removable sub-top. The tongs can then be stowed in the sub-top or at the top of the body portion, so that they are visible and readily accessible on removal of the sub-top. The sub-top can be, for example, a press fit on, hinged to, or screwed on, the body portion of the cap. Removal of the sub-top can make it easier, or possible, to use the body portion of the cap to connect the retaining collar to the neck of the feed container without the need to handle the collar, as previously described.

Preferably, the feed dispensing means, when disposed in the cap, can be engaged with the container for assembly of the feed container without the need for other contact with the feed dispensing means. When a sub-top is provided, said feed dispensing means may be engaged with the feed container through an opening of the cap to which the sub-top is connected.

Moreover, the retaining collar, when disposed in the cap, can preferably be engaged with the container for assembly of the feed container without the need for other contact with the retaining collar. In this event, said retaining collar and cap may have respective interengagable detent means preventing relative rotation thereof, whereby rotation of the cap permits screw-threading of the collar onto the threaded portion of the neck of the container.

In still another preferred embodiment of the invention, the sealing disc is stowed within the cap in such a manner that it blocks the outlet of the feed dispensing means when the feed dispensing means is connected to the feed container. Thus if the feed container containing liquid feed should be knocked over, the sealing disc can prevent or reduce the loss of liquid feed through the outlet of the feed dispensing means. This is yet another separate aspect of the invention. In this embodiment, the sealing disc and the tongs are both preferably stowed in the sub-top. The sealing disc is preferably stowed in the sub-top in such a manner that it can be dislodged by tilting, for example, by applying pressure to one side of a face of the disc.

BRIEF DESCRIPTION OF THE DRAWINGS

A number of preferred embodiments of the invention will now be described, by way of example, with reference to the accompanying drawings, in which:

FIG. 2a shows the assembled bottle in sectional side elevation; FIG. 2b shows a view inside a cap shown in FIG. 2b in the direction of arrow a, with the teat removed showing the positions of the sealing disc, tongs and threaded collar;

FIGS. 4a and 4b show a further embodiment of an oral feeding bottle according to the invention; FIG. 4a shows the assembled bottle in sectional side elevation; FIG. 4b is a fragmentary sectional side elevation which shows an alternative dormal cap ejector for the cap of FIG. 4a;

FIGS. 5a–5d show a still further embodiment of an oral feeding bottle of the invention, wherein the cap is provided with a removable sub-top; FIG. 5a shows the oral feeding bottle in feeding mode; FIG. 5b shows the same bottle in sterilising mode; FIG. 5c shows a view inside the sub-top of the cap of FIG. 5a in the direction of arrow b; and FIG. 5d shows the tongs when released from the cap;

FIGS. 6a–6e show a still further embodiment of an oral feeding bottle according to the invention; FIG. 6a shows the bottle in feeding mode; FIG. 6b shows the bottle in sterilising mode; FIG. 6c shows a view inside the sub-top of the cap of the bottle; FIG. 6d shows the sub-top of the cap in sectional side elevation; and FIG. 6e shows the tongs when removed from the sub-cap;

FIGS. 7a–7e show another embodiment of an oral feeding bottle according to the invention in sectional side elevation; FIG. 7a shows the bottle in feeding mode; FIG. 7b shows the bottle inverted and in sterilising mode; FIG. 7c shows a plan view of the cap in the direction of arrow c; FIG. 7d shows the tongs when released from the cap; and FIG. 7e shows the sealing disc in sectional side elevation; and FIGS. 8a–8c show still another embodiment of an oral feeding bottle according to the invention in sectional side elevation; FIG. 8a shows the bottle in feeding mode; FIG. 8b shows the bottle inverted and in sterilising mode; and FIG. 8c shows the tongs when released from the cap.

FIGS. 9a–9d show yet another embodiment of an oral feeding bottle according to the invention in sectional side elevation; FIG. 9a shows the bottle in feeding mode; FIG. 9b illustrates the bottle in sterilising mode; FIG. 9c shows a section of the sub-top along the line A—A, and also shows the removal of the sealing disc from the sub-top; and FIG. 9d illustrates the removal of the sub-top from the cap.

DETAILED DESCRIPTION OF THE INVENTION

Figure 1:
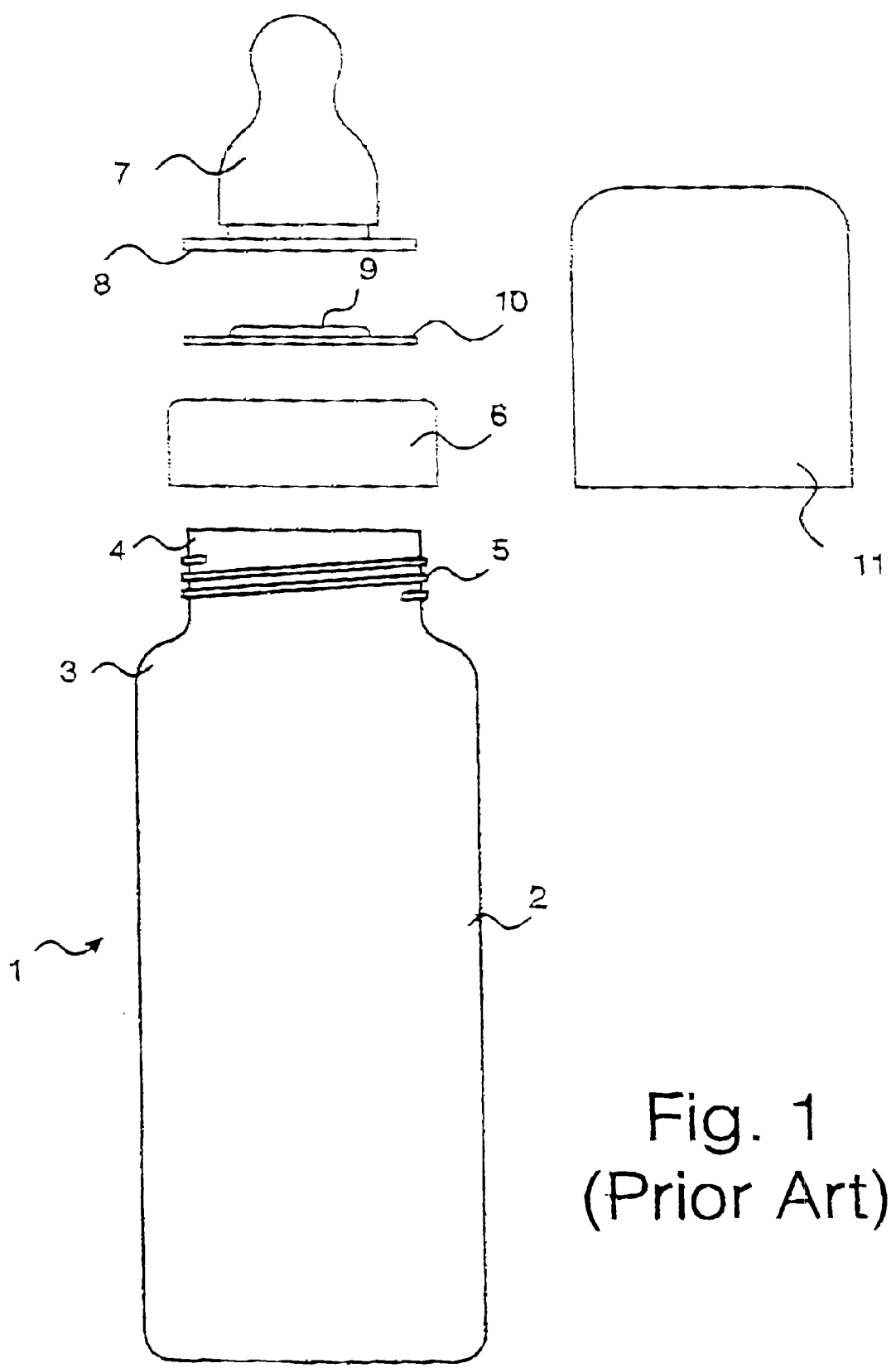
FIG. 1 shows a prior art oral feeding bottle in exploded side elevation.

Referring now to the drawings, FIG. 1 shows a typical conventional infant oral feeding bottle, illustrated generally at 1. The bottle comprises a transparent plastics feed container 2 which is of generally cylindrical shape and has a shoulder 3 leading to a neck portion 4 provided with a threaded section 5. Co-operable with the threaded section 5 is a threaded collar 6 adapted to receive within a central aperture of the collar a flexible rubber or plastics teat 7 and to engage with a flange 8 on the teat 7. Also provided is a sealing disc 9 with a flange 10 which can also engage with the threaded collar 6 when the bottle is not in use. The teat 7 is in this case inverted and lies inside the bottle 2, the flange acting as a seal between the neck 4 and disc flange 10. Finally, the teat and collar assembly can be surmounted by a dormal cap 11 which is a press fit on the outside of the threaded collar 6.

Figure 2B:
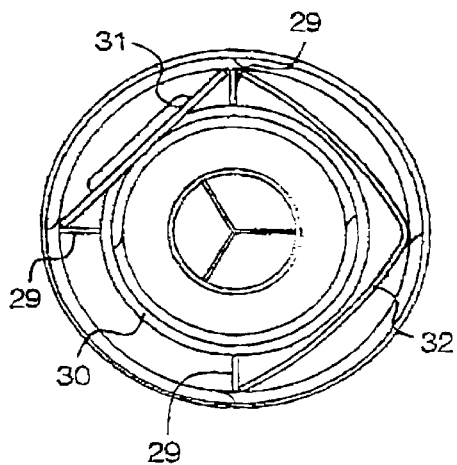
FIGS. 2a and 2b show a first embodiment of an oral feeding bottle according to the invention.
Figure 2A:
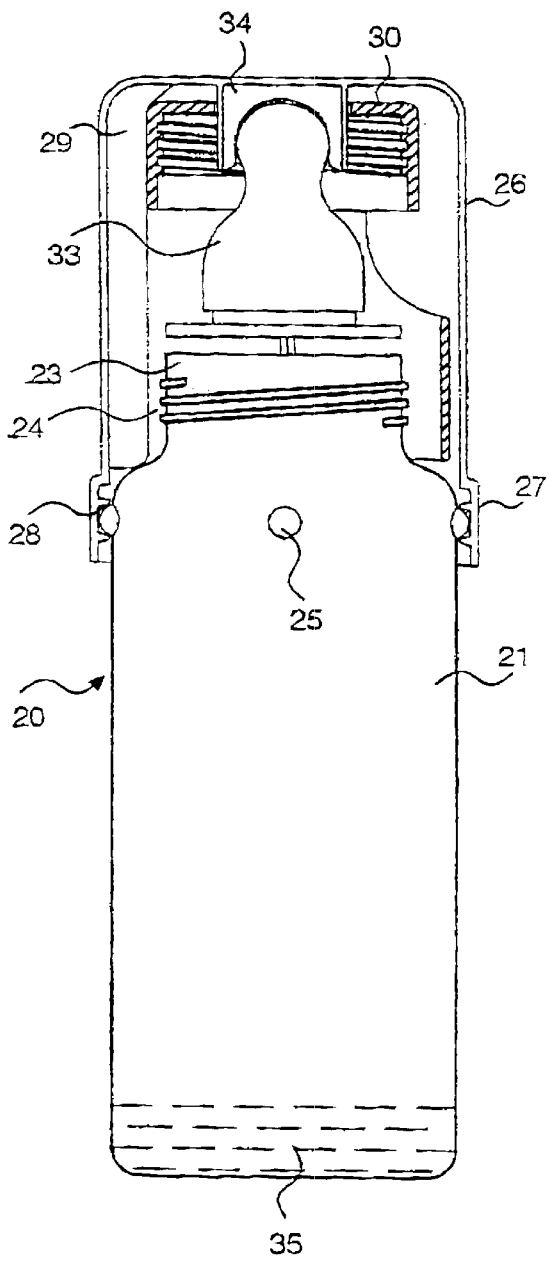

Referring now to FIGS. 2a and 2b, there is shown a first embodiment of an oral feeding bottle according to the invention, illustrated generally at 20. The bottle comprises a feed container 21 of generally cylindrical shape, having a shoulder 22 and a neck portion 23 with a threaded section 24. Below the shoulder 22 are a series of circumferentially positioned projections 25 which act as press fit locating points for a cap 26. The cap 26 has a lip 27 with an internal groove 28 co-operable with the projections 25 so that the cap is a press fit on the feed container 21.

Within the cap, longitudinally extending webs 29 receive threaded collar 30, and serve to locate sealing disc 31 and flexible tongs 32. Teat 33 is located in the cap by gripper means 34.

It can be seen that the components of the oral feeding bottle, other than the feed container, are disassembled and located within the cap 26 in such a manner that their surfaces are exposed for sterilisation. The threaded region 24 of the feed container is also available to be sterilised.

In use, a small quantity of water 35 is placed in the feed container 21 and the cap and components located in position. The bottle can then be placed in a microwave oven and the water 35 heated to create steam which rises into the cap and sterilises the components located therein. Build up of excess steam pressure is vented through the annular space between the grooved lip 27 and the exterior wall of the feed container 21.

Figure 3:
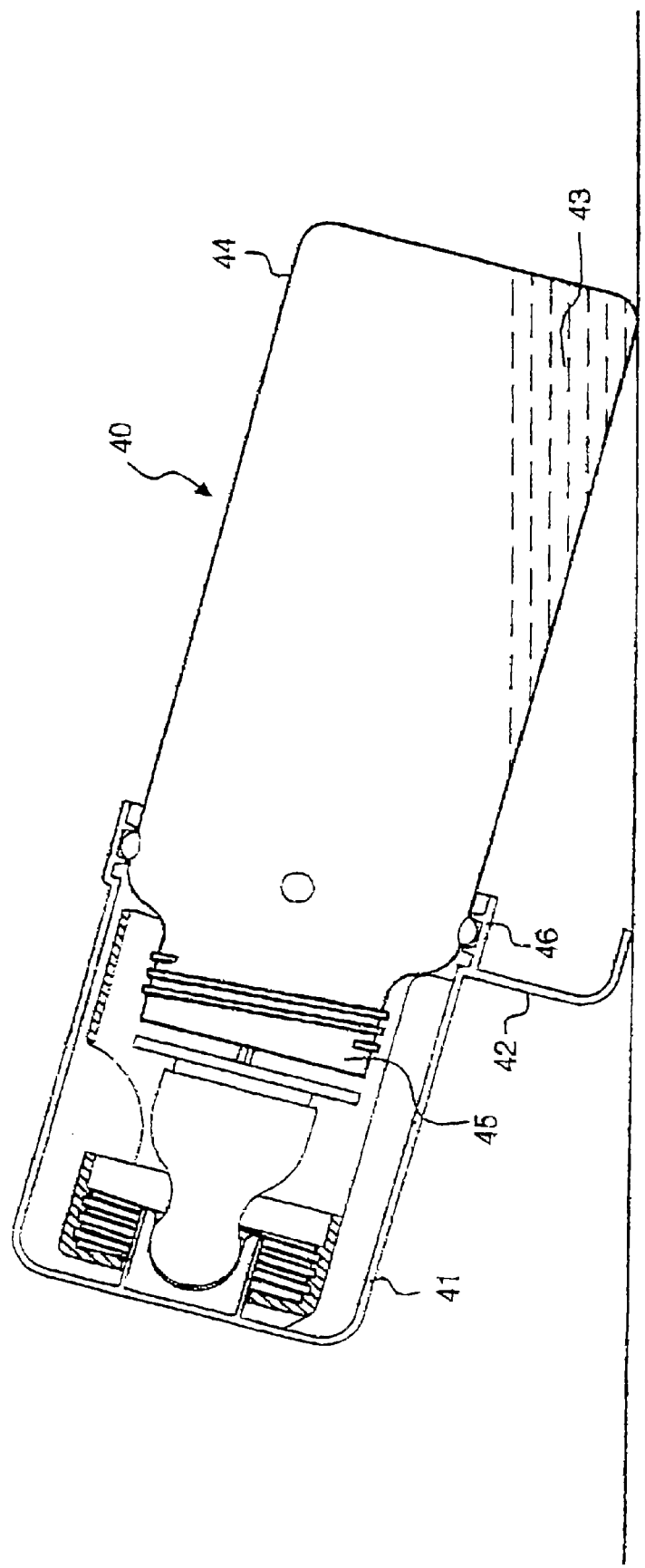
FIG. 3 shows a second embodiment of an oral feeding bottle according to the invention in sectional side elevation and in the sterilising mode.

The oral feeding bottle shown in FIG. 3 and illustrated generally at 40, is similar to that of FIGS. 2a and 2b, except that the cap 41 is provided with a laterally extending leg 42 on which the feeding bottle 40 can be stood at an angle to the horizontal. This permits the feeding bottle to be stood on its side without the risk that the water 43 disposed in the feed container 44 will escape via the neck 45 and past the lip 46.

An embodiment of a cap according to the invention, which can be used with a conventional oral feeding bottle, is illustrated in FIGS. 4a and 4b. The oral feeding bottle, illustrated generally at 50, comprises a conventional feed container 51 having a shoulder 52, a neck 53 and a threaded neck section 54. Also illustrated are threaded collar 55, teat 56 and dormal cap 57 of the conventional oral feeding bottle. The cap of the invention 58 is seated upon means for stowing the cap in the form of a grid 59 which has a collar 60 which has a small clearance over the threaded section 54 of the feed container 51, and rests upon the shoulder 52. The grid may be retained on the feed container, for example, by projecting lugs 73. The grid 59 has an upstanding cone-shaped web 61 upon which the threaded collar 55 is seated, and has a central pillar 62 for locating the teat 56. The dormal cap 57 is held in position by webs 63 on the cap 58.

The cap 58 is also provided with a dormal cap ejector 64, 65, two embodiments of which are illustrated in FIGS. 4a and 4b. In each case, pressure on the flexible domed section, 66, 67 forces a pin 68, 69 into the cap and into contact with the top of the dormal cap 57, thereby ejecting it from the cap 58. In FIG. 4a the dormal cap ejector 64 is integral with the cap 58, whereas in FIG. 4b the dormal cap ejector 65 is a separate part and the pin 69 passes through a hole 70 in the recessed top 71 of the cap 72.

Turning now to FIGS. 5a–5d, there is shown a compact version of an oral feeding bottle according to the invention. The bottle, illustrated generally at 80 has a feed container 81, of generally cylindrical shape, having a shoulder 82, and a neck portion 83, with a threaded section 84. A threaded collar 85 co-operates with the threaded section 84 and retains the flange 86 of a teat 87 on the neck of the feed container 81. The bottle is provided with a cap 88, which in this case also acts as a dormal cap. The cap is formed from a plastics material and is in two parts, a lower cylindrical section 89 and an upper sub-top 90. The parts 89 and 90 are a press fit together. A sealing disc 91 and tongs 92 are located inside the cap as shown, and, in the case of the sealing disc, location is provided by webs 93 extending from the wall of the cap.

In feeding mode, the oral feeding bottle is shown in FIG. 5a. To provide the feed to the infant it is merely necessary to remove the cap 88 together with the components located therein.

In sterilising mode, the threaded retaining collar 85 is removed together with the teat 87. These are both then located within the cap 88, in the case of the teat 87 in an inverted position. A small quantity of water 94 is then placed in the feed container 81 and the cap 88 replaced, the lip 95 of the cap locating on a projecting collar 96 on the neck 83 of the feed container 81. Again it can be seen that all the components of the oral feeding bottle are disposed within the cap in such a manner that steam from the boiling water in the feed container can easily reach all the surfaces of the components. The cap 88 is formed in two parts for ease of manufacture and also in order to enable the sub-top 90 to be removed for ready removal of the tongs 92 and the sealing disc 91. The tongs 92, shown open in FIG. 5d, are retained in the cap 88 by resilient opening pressure of the tongs against the inside walls of the sub-top.

FIGS. 6a–6e show another embodiment of an oral feeding bottle according to the invention, this time of standard height. The feeding bottle, illustrated generally at 100, is substantially identical to the bottle of FIG. 5, and is similarly provided with a two-part cap 101 of which a sub-top 102 is removable. The stowage of the components within the cap 101 for sterilisation is substantially the same as that shown in FIG. 5.

Extending collar 103, upon which the cap 101 is a press fit, is provided with recessed cut-out portions 104 around its circumference, in order to allow for the venting of excess steam and water. The rim of the cap 105 is only a loose fit on the shoulder 106 of the feed container 107, and thus steam passing through the cut out portions 104 can easily vent to the atmosphere.

A further embodiment of an oral feeding bottle according to the invention is shown in FIG. 7 FIGS. 7a–7e. Again, the feeding bottle, illustrated generally at 120 comprises a feed container 121 and a cap 122. As illustrated in FIG. 7a, in feeding mode a sealing disc 123 is removed and optionally also arcuate tongs 1124. The cap 122 acts as a conventional dormal cap and is removed for feeding.

In sterilising mode, the components are assembled and stowed in the cap 122 as shown in FIG. 7b, with the sealing disc 123 and threaded retaining collar 124 located on circumferential webs 125 formed by scalloped indentations in the peripheral wall of the cap 122. The teat 126 rests on projections 127 on the threaded collar 124, and the tongs 1124 rest against a detent 128 in the wall of the cap 122.

In sterilising mode, a small quantity of water 129 is placed in the cap, which can have a fill level indicator and the container, cap and components are assembled together. The bottle 120 is then placed in a microwave oven for sterilisation in the same manner as previously described.

FIGS. 8a–8c show a further embodiment of a standard size bottle fitted with a cap according to the invention. The bottle, illustrated generally at 130, is fitted with a cap 131 similar to that shown in FIGS. 7a–7e. As before, the cap provides means for locating sealing disc 132, threaded collar 133 and teat 134 in inverted positions, and provides a peripheral location for flexible arcuate tongs 135. As with the embodiment of FIGS. 7a–7e, the bottle of FIGS. 8a–8c is inverted in order to carry out the sterilisation procedure.

FIGS. 9a–9d show a further embodiment of an oral feeding bottle according to the invention, illustrating the function of the sealing disc and its removal from the sub-top, and also the use of the body portion of the cap to screw the retaining collar onto the threaded neck portion of the feed container.

FIG. 9a shows an oral feeding bottle illustrated generally at 140 comprising a feed container 141 and a cap of the invention 142, which in this case also fulfils the function of a dormal cap. The cap 142 has a body portion 143 and a sub-top 144.

A teat 145 is connected to the feed container 141 by a threaded collar 146 which engages with a threaded portion 147 on the neck 148 of the feed container 141. In the feeding mode, as illustrated in FIG. 9a sealing disc 149 is stowed within the sub-top 144 and rests on webs 150 and 151. In this position, it blocks the hole or holes 152 at the top of the teat 145, thus preventing any liquid feed from spilling out of the teat if the bottle is knocked over.

The sub-top 144, which is either a snap-fit, or is screwed, hinged or pivoted to the body portion 143, can be removed as illustrated in FIG. 9d. Removal of the sub-top 144 exposes the sealing disc 149 for removal. The sealing disc 149 can be removed by pressure on the edge surface 162, which causes the sealing disc to pivot about the webs 150 and dislodges the disc from frictional engagement with the webs 151. The sealing disc can then be removed.

The position of the components in the sterilising mode is shown in FIG. 9b. Both the retaining collar 146 and the teat 145 are located by means of webs 153. By a suitable shaping of the wall 154 of the body portion of the cap 142 such that it is an interference fit with the threaded retaining collar 146, it would be possible to use the body portion of the cap to screw the threaded collar 146 onto the threaded portion 147 of the neck of the feed container 140. In use, the body portion 154 as illustrated in FIG. 9b would first be detached from the sub-top 144 and inverted over the feed container 141 in order to place the teat 145 on the neck 148 of the feed container. (Alternatively, tongs (not shown in FIGS. 9a–9d) could be employed to place the teat inverted in the bottle for its transportation mode, whereupon the sealing disc 149 is placed on top of the flange 163 of the teat). In either event, the body portion is then inverted again, and placed over the teat (or sealing disc) in order to bring the threaded collar 146 in register with the neck 148 of the feed container. Turning the body portion 154 screws the threaded collar 146 onto the threaded portion 147 of the neck 148, thereby securing the teat 145 to the feed container. For this purpose, some detent means, (not shown) is provided to prevent relative rotation of the cap and collar when the collar is stowed in the cap.

A clearance 164 is provided between lip 166 of the cap body 154 and shoulder 168 of the bottle 141 to enable some vertical movement of the cap body 154 and collar 146 while their threads engage. Thereafter, the threads themselves will draw the collar down as the collar is screwed on. Also, lip 166 needs to be sufficiently distanced from the webs 153 to enable it to snap over detent lip 170 of the bottle 141, even when the respective ends of the threads on the collar and bottle neck are in register with one another.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification including any accompanying claims, abstract and drawings, and/or all of the steps of any method or process so disclosed, may be combined in any combination, except combinations where at least some of such features and/or steps are mutually exclusive.

Each feature disclosed in this specification including any accompanying claims, abstract and drawings, may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification including any accompanying claims, abstract and drawings, or to any novel one, or any novel combination, of the steps of any method or process so disclosed.

What is claimed is:

1. An oral feeding bottle comprising:
   a) a feed container having an open end, surfaces adapted to come into contact with a liquid feed residing in said container, and first connection elements disposed around said open end;
   b) a teat, having internal and external surfaces, a flange for connection to said open end and an aperture through which said liquid feed is dispensed, said teat when releasably connected to said open end of said feed container is adapted to come into contact with both the liquid feed residing in said feed container and a person or animal feeding from the bottle; and
   c) a cap, having a rim, second connection elements around said rim and stowing formations spaced from said rim, said cap has a first mode and a second mode of operation and during both modes it is releasably connected to said feed container by inter-engagement of said first and second connection elements, wherein:

in said first mode of operation of said cap, said teat is connected to said feed container in a dispensing position thereof, said cap fits over and encloses the teat; and in the second mode of operation of the cap, said teat is seated on said stowing formations in a non-dispensing position of said teat spaced from said feed container, said stowing formations being disposed around the inside of said cap so that spaces are defined therebetween and between the teat and the cap, whereby the internal and external surfaces of said teat, and the surface of the feed container that contact the liquid feed, are in fluid communication with each other, at least through said spaces, so that sterilization of said teat and said feed container can be carried out with a fluid sterilizing medium disposed in said feed container or said cap.

2. An oral feeding bottle according to claim 1, further comprising a plurality of components of the bottle other than said feed container, said teat and said cap, and wherein said cap has means for stowing said plurality of components.

3. An oral feeding bottle according to claim 2, wherein the plurality of components comprises a retaining collar and a sealing disc.

4. An oral feeding bottle according to claim 2, wherein the plurality of components further comprises a pair of tongs.

5. An oral feeding bottle according to claim 1, wherein the open end of the feed container comprises a neck with a threaded portion, and the teat is connectable to the feed container by a threaded collar which engages with the threaded portion of the neck of the feed container.

6. An oral feeding bottle according to claim 5, wherein, when the cap is connected to the feed container in said second mode, the threaded portion of the neck of the feed container is exposed to the sterilizing medium.

7. An oral feeding bottle according to claim 1, wherein said stowing formations comprises one or more webs extending from the wall of the cap.

8. An oral feeding bottle according to claim 1, further comprising a means for venting to allow the escape of steam from an interior area of the feeding bottle.

9. An oral feeding bottle according to claim 8, wherein the means for venting comprises holes or apertures in the cap.

10. An oral feeding bottle according to claim 8, wherein the means for venting comprises passageways between the cap and the exterior surface of the feed container.

11. An oral feeding bottle according to claim 1, wherein the teat is inverted with respect to the feed container when stowed in the cap in said second mode of operation.

12. An oral feeding bottle according to claim 1, wherein said inter-engagement of said first and second connection means is a direct connection between said feed container and cap.

13. An oral feeding bottle according to claim 12, wherein said first and second connection elements are a continuous groove on one of said cap and said feed container and spaced projections on the other of said cap and said feed container adapted to snap into engagement with said groove.

14. An oral feeding bottle according to claim 1, further comprising a grid having a collar, and wherein during said second mode of operation said inter-engagement of said first and second connection elements is an indirect connection between said feed container and said cap, said collar of said grid engaging with said feed container and said cap being seated on said grid.

15. An oral feeding bottle according to claim 1, wherein a retaining collar is provided to secure said teat to said feed container in said first mode of operation of said cap, and wherein said teat is supported on said stowing formations in said second mode of operation of said cap through said retaining ring seated on said stowing formations.

16. An oral feeding bottle according to claim 1, wherein said stowing formations comprises one or more projections extending from the wall of the cap.

17. An oral feeding bottle according to claim 1, wherein said stowing formations comprises one or more indents extending from the wall of the cap.

18. An oral feeding bottle according to claim 1, wherein said stowing formations comprises one or more ledges extending from the wall of the cap.

19. An oral feeding bottle according to claim 1, wherein said stowing formations comprises one or more shoulders extending from the wall of said cap.

20. An oral feeding bottle according to claim 1, which can be inverted in order to stand with the cap as its base.

21. An oral feeding bottle according to claim 1, that is made entirely from microwave oven stable components.

22. An oral feeding bottle comprising:

a) a feed container having an open end, surfaces adapted to come into contact with a liquid feed residing in said feed container, and first connection elements disposed around said open end;

b) a teat, having internal and external surfaces, a flange for connection to said open end and an aperture through which said liquid feed is dispensed, said teat when releasably connected to said open end of said feed container is adapted to come into contact with both the liquid feed residing in the container and a person or animal feeding from the bottle; and c) a cap, having a rim, second connection elements around said rim and stowing formations spaced from said rim, said cap has a first and a second mode of operation wherein said cap is releasably connected to said feed container in both said modes of operation through direct inter-connection of said first connection elements of said feed container with said second connection elements of said cap, and wherein:

in said first mode of operation of said cap, said teat is connected to said feed container in a dispensing position thereof, said cap fits over and encloses said teat; and in said second mode of operation of said cap, said teat is seated on said stowing formations in a non-dispensing position of said teat spaced from said feed container, whereby said internal and external surfaces of said teat, and the surface of said feed container that contact the liquid feed, are in fluid communication with each other, so that sterilization of said teat and said feed container can be carried out with a fluid sterilizing medium disposed in said feed container or cap.

23. An oral feeding bottle according to claim 22, wherein said first and second connection elements are a continuous groove on one of said cap and feed container and spaced projections on the other of said cap and feed container adapted to snap into engagement with said groove.

* * * * *